United States Patent
Tsujita et al.

(10) Patent No.: US 8,758,327 B2
(45) Date of Patent: Jun. 24, 2014

(54) MANIPULATOR AND MANIPULATION DEVICE EQUIPPED WITH IT

(75) Inventors: Teppei Tsujita, Sendai (JP); Kosuke Kishi, Mito (JP); Makoto Hashizume, Kasuga (JP)

(73) Assignees: Hitachi, Ltd., Tokyo (JP); Kyushu University, Fukuoka (JP)

( * ) Notice: Subject to any disclaimer, the term of this patent is extended or adjusted under 35 U.S.C. 154(b) by 1771 days.

(21) Appl. No.: 12/141,199

(22) Filed: Jun. 18, 2008

(65) Prior Publication Data

US 2008/0310945 A1    Dec. 18, 2008

(30) Foreign Application Priority Data

Jun. 18, 2007   (JP) .................................. 2007-159875

(51) Int. Cl.
*A61M 25/082*   (2006.01)
*A61M 25/08*    (2006.01)

(52) U.S. Cl.
USPC ..................................... 604/528; 604/164.12

(58) Field of Classification Search
USPC .............. 74/490.01; 604/528, 164.01, 164.12
See application file for complete search history.

(56) References Cited

U.S. PATENT DOCUMENTS 7,955,316 B2 *   6/2011   Weitzner et al. .............. 604/528
2012/0071822 A1 *  3/2012   Romo et al. ................ 604/95.04

FOREIGN PATENT DOCUMENTS

| EP | 1 679 046 A2 | 7/2006 |
|---|---|---|
| JP | 1 281 883 A | 11/1989 |
| JP | 06-042601 | 2/1994 |
| JP | 09-285989 | 11/1997 |
| JP | 2003-534038 | 11/2003 |
| JP | 2006-191939 | 7/2006 |
| WO | WO 01/74259 A1 | 10/2001 |

OTHER PUBLICATIONS

Search Report of EP Appln. No. 08010984.6 dated May 26, 2011 in English.
Japanese office action of Appln. No. 2007-159875 dated Oct. 25, 2011.

* cited by examiner

*Primary Examiner* — David M Fenstermacher
*Assistant Examiner* — Terence Boes
(74) *Attorney, Agent, or Firm* — Antonelli, Terry, Stout & Kraus, LLP.

(57) ABSTRACT

The invention provides a manipulator which can carry out a treatment having a large moving amount in a manipulator leading end while being compact. The manipulator is provided with a manipulator shaft portion, a first rod supported so as to be capable of linearly moving with respect to the manipulator shaft portion and driven by a driving force of a driving source, a first gear rotatably supported to the first rod, a first rack supported to the manipulator shaft portion, a second rack supported so as to be capable of linearly moving in the same direction as the first rod with respect to the manipulator shaft portion, and a end-effecter driven by the driving force of the second rack. The first rack and the second rack are arranged in such a manner that respective cogged surfaces come face to face. The first gear is pinched between the first rack and the second rack, and is arranged in an engaged state.

9 Claims, 12 Drawing Sheets

MANIPULATOR AND MANIPULATION DEVICE EQUIPPED WITH IT

BACKGROUND OF THE INVENTION (1) Field of the Invention

The present invention relates to a manipulator and a manipulation device using the same, and more particular to a compact manipulator for a medical application and a manipulation device using the same.

(2) Description of Related Art

A high-frequency end-effecter is bored into a body of a patient while observing an affected part by using a diagnosis apparatus such as an MRI, an ultrasonic scanner, an endoscope or the like, thereby treating the affected part within a body cavity.

Further, for example, JP-A-2003-534038 (patent document 1) describes a manipulation device (a medical apparatus) provided with a guide portion accommodating a puncture needle and a driving apparatus of the puncture needle, in which a guide portion is divided into two portions, a puncture needle is friction bonded between the two portions by a driving roller, and a motor is driven in accordance with a remote control, thereby enabling a linear movement sticking a end-effecter from a body surface of a patient.

Further, for example, JP-A-09-285989 describes a multistage telescopic apparatus for obtaining a great linear moving amount while having a small installed space.

In the prior art mentioned above, it is necessary to bore the needle in a narrow space within a gantry of the diagnosis apparatus such as the MRI or the like, and it is required to downsize more.

Further, in the structure described in the patent document 1, the puncture can be carried out in accordance with a remote control, however, it is hard to correspond to the other treatment than the puncture. Further, since the end-effecter is linearly inserted to the affected portion from the body surface of the patient, there is a case that it is hard to insert while avoiding the other internal organ, blood vessel or the like (hereinafter, refer to as an obstacle) which should not be injured than the affected portion.

Further, in order to correspond to various treatments, it is necessary to attach and detach plural kinds of manipulators to and from a driving mechanism so as to replace, however, in the case that the driving apparatus such as the motor or the like is installed in the driving mechanism, the structure is enlarged in size and is not suitable for being used in a narrow space such as within the gantry or the like. Further, there is a case that an influence of a noise or the like is applied to the diagnosis apparatus, by installing the driving apparatus within the gantry.

Accordingly, there can be considered a method of transmitting a driving force of the driving apparatus by using a wire from an external portion such as an outer side of the gantry of the diagnosis apparatus or the like, however, in the case of using the wire, there is a case that a controllability is deteriorated by a slack of the wire or the like, or a problem of a fatigue disconnection of the wire is generated.

Further, in order to downsize the driving mechanism, it is necessary to make a moving amount for driving the manipulator which can be replaced from the removable portion small. Accordingly, there is a risk that the moving amount runs short in a manipulator leading end with respect to an operation device carrying out the treatment.

In order to sufficiently enlarge the moving amount in the manipulator leading end, it is preferable to amplify the moving amount until the leading end in comparison with the moving amount of the driving, however, in the case of simply applying the multistage telescopic apparatus as described in the patent document 2, a force necessary for driving the telescopic mechanism is increased in an equal rate to an amplification factor of a linear moving amount, and it is hard to achieve a great linear motion force.

BRIEF SUMMARY OF THE INVENTION

An object of the present invention is to provide a manipulator which can enlarge a moving amount of an end-effecter in a manipulator leading end while being compact, and a manipulation device using the same.

In order to achieve the object mentioned above, in accordance with a first aspect of the present invention, there is provided a manipulator comprising:

a manipulator shaft portion;

a first rod supported so as to be capable of linearly moving with respect to the manipulator shaft portion and driven by a driving force;

a first gear rotatably supported to the first rod and moved in accordance with a movement of the first rod;

a first rack fixed to the manipulator shaft portion;

a second rack supported so as to be capable of linearly moving in the same direction as the first rod with respect to the manipulator shaft portion; and an end-effecter driven by the driving force generated in accordance with a movement of the second rack, wherein the first rack and the second rack are arranged in parallel in such a manner that a cogged surface of the first rack and a cogged surface of the second rack come face to face, and the first gear is pinched between the first rack and the second rack, and is arranged in a state of engaging with each of the first rack and the second rack.

A more preferable specific structure example in the first aspect of the present invention mentioned above is as follows.

(1) The manipulator is provided with a second rod supported so as to be capable of linearly moving with respect to the manipulator shaft portion and driven by the driving force, a second gear rotatably supported to the second rod, and a third rack supported so as to be capable of linearly moving in the same direction as the second rod with respect to the manipulator shaft portion, wherein the second rack and the third rack are arranged in parallel in such a manner that a cogged surface of the second rack and a cogged surface of the third rack come face to face, the second gear is pinched between the second rack and the third rack, and is arranged in a state of engaging with each of the second rack and the third rack, and the end-effecter is driven by a driving force generated in accordance with the movement of the third rack.

(2) Plural sets of mechanisms are provided in line, the mechanism comprising the second rack, the second rod, the second gear and the third rack.

(3) A manipulator bending portion bending the manipulator is provided in an intermediate portion of the manipulator, and the manipulator bending portion has a transmission mechanism for bending drivingly transmitting the linear motion by the second rack to a leading end portion of the manipulator via the manipulator bending portion.

(4) The transmission mechanism for bending has a first linear motion transmitting gear converting the linear motion by the second rack into a rotating motion, a first pulley provided coaxially with the first linear motion gear and synchronously rotating with the first linear motion transmission gear, a timing belt transmitting the rotating motion of the first pulley to the second pulley, a second linear motion transmitting gear provided coaxially with the second pulley and synchronously rotating with the second pulley, a third linear motion transmission gear provided so as to be engaged with the second linear motion transmitting gear, a fourth linear motion transmitting gear provided so as to be engaged with the third linear motion transmitting gear, a rack gear provided coaxially with the fourth linear motion transmitting gear, rotating synchronously with the linear motion transmitting gear and having a flexibility, and a rack converting the rotating motion of the rack gear having the flexibility into the linear motion so as to generate the driving force applied to the end-effecter and having a flexibility.

(5) The leading end portion of the manipulator is replaceable.

Further, in accordance with a second aspect of the present invention, there is provided a manipulator comprising:

a manipulator shaft portion;

a first rod supported so as to be capable of linearly moving with respect to the manipulator shaft portion and driven by a driving force;

a first roller rotatably supported to the first rod and moved in accordance with a movement of the first rod;

a first plate fixed to the manipulator shaft portion;

a second plate supported so as to be capable of linearly moving in the same direction as the first rod with respect to the manipulator shaft portion; and an end-effecter driven by the driving force generated in accordance with a movement of the second plate, wherein the first plate and the second plate are arranged in parallel in such a manner that respective surfaces come face to face, and the first roller is pinched between the first plate and the second plate, and is arranged in a state of coming into rolling contact with each of the first plate and the second plate.

Further, in accordance with a third aspect of the present invention, there is provided a manipulation device comprising:

a manipulator; and a driving apparatus driving the manipulator, wherein the manipulator comprises:

a manipulator shaft portion;

a first rod supported so as to be capable of linearly moving with respect to the manipulator shaft portion and driven by a driving force of the driving apparatus;

a first gear rotatably supported to the first rod and moved in accordance with a movement of the first rod;

a first rack fixed to the manipulator shaft portion;

a second rack supported so as to be capable of linearly moving in the same direction as the first rod with respect to the manipulator shaft portion; and an end-effecter driven by the driving force generated in accordance with a movement of the second rack, and wherein the first rack and the second rack are arranged in parallel in such a manner that a cogged surface of the first rack and a cogged surface of the second rack come face to face, and the first gear is pinched between the first rack and the second rack, and is arranged in a state of engaging with each of the first rack and the second rack.

A more preferable specific structure example in the third aspect of the present invention mentioned above is as follows.

(1) A removable mechanism is provided in the manipulator side, a removable driving mechanism is provided in the driving apparatus side, and the removable mechanism in the manipulator side is detachable with respect to the removable driving mechanism in the driving apparatus side.

(2) The manipulator is provided with a second rod supported so as to be capable of linearly moving with respect to the manipulator shaft portion and driven by the driving force, a second gear rotatably supported to the second rod, and a third rack supported so as to be capable of linearly moving in the same direction as the second rod with respect to the manipulator shaft portion, wherein the second rack and the third rack are arranged in parallel in such a manner that a cogged surface of the second rack and a cogged surface of the third rack come face to face, the second gear is pinched between the second rack and the third rack, and is arranged in a state of engaging with each of the second rack and the third rack, and the end-effecter is driven by a driving force generated in accordance with the movement of the third rack.

In accordance with the manipulator of the present invention and the manipulation device using the same, it is possible to enlarge a moving amount of the end-effecter in a leading end of the manipulator while being compact in size.

Other objects, features and advantages of the invention will become apparent from the following description of the embodiments of the invention taken in conjunction with the accompanying drawings.

DETAILED DESCRIPTION OF THE INVENTION

A description will be given below of an embodiment in accordance with the present invention with reference to FIGS. 1 to 15.

Figure 1:
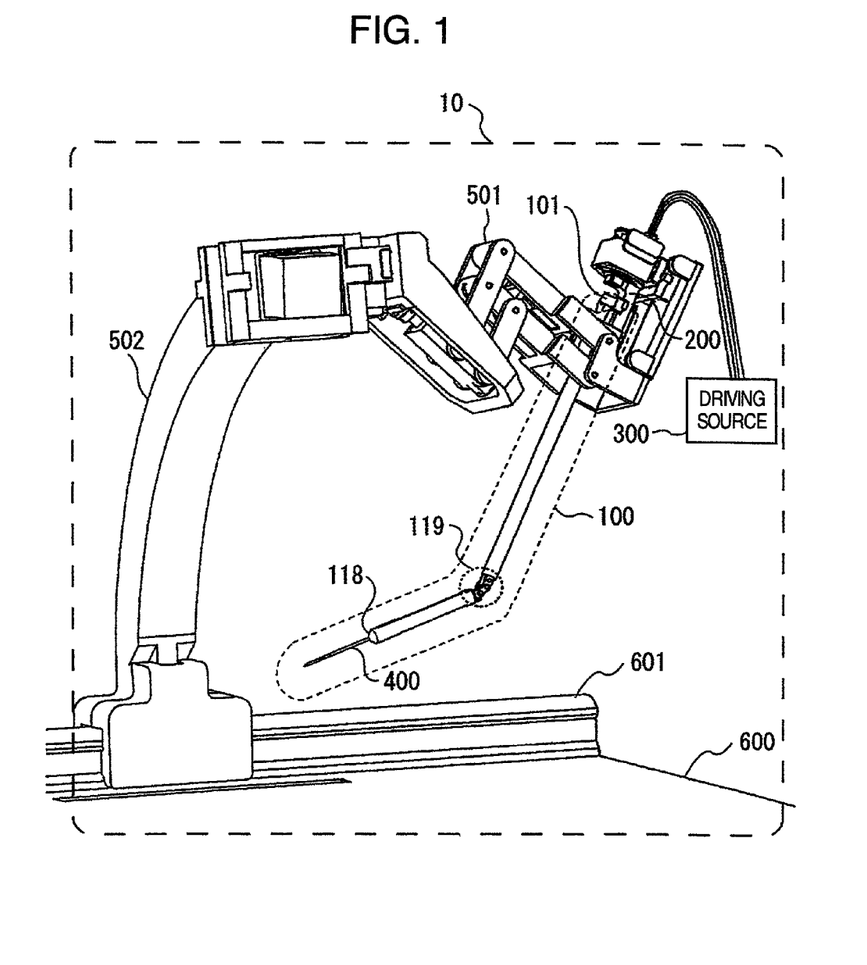
FIG. 1 is a perspective view of a manipulation device in accordance with an embodiment of the present invention.

FIG. 1 is a perspective view of a manipulation device 10 in accordance with the present embodiment. The manipulation device 10 is constituted by a manipulator 100, a driving apparatus, a link mechanism 500 and the like, and is structured such as to correspond to various treatments by replacing a plurality of manipulators 100. The driving apparatus is constituted by a removable driving mechanism 200, a driving source 300 and the like.

The manipulator 100 is provided with a manipulator bending portion 119. Accordingly, the manipulator 100 has a freedom avoiding an obstacle. The manipulator bending portion 119 is provided in an intermediate portion of the manipulator 100. A needle 400 corresponding to a end-effecter is stored in an inner portion of the manipulator 100, from a manipulator leading end portion 118 to the manipulator bending portion 119. The needle 400 is arranged so as to be linearly moved by the manipulator 100 and be taken in and out of the manipulator leading end portion 118. Further, the manipulator 100 is connected to the removable driving mechanism 200 via the removable mechanism 101.

The removable driving mechanism 200 is supported to a rail 601, for example, installed in a bed 600, via a link mechanism 501 and an arm 502. A lower end portion of the arm 502 is fixed to the rail 601 so as to be installed.

Figure 2:
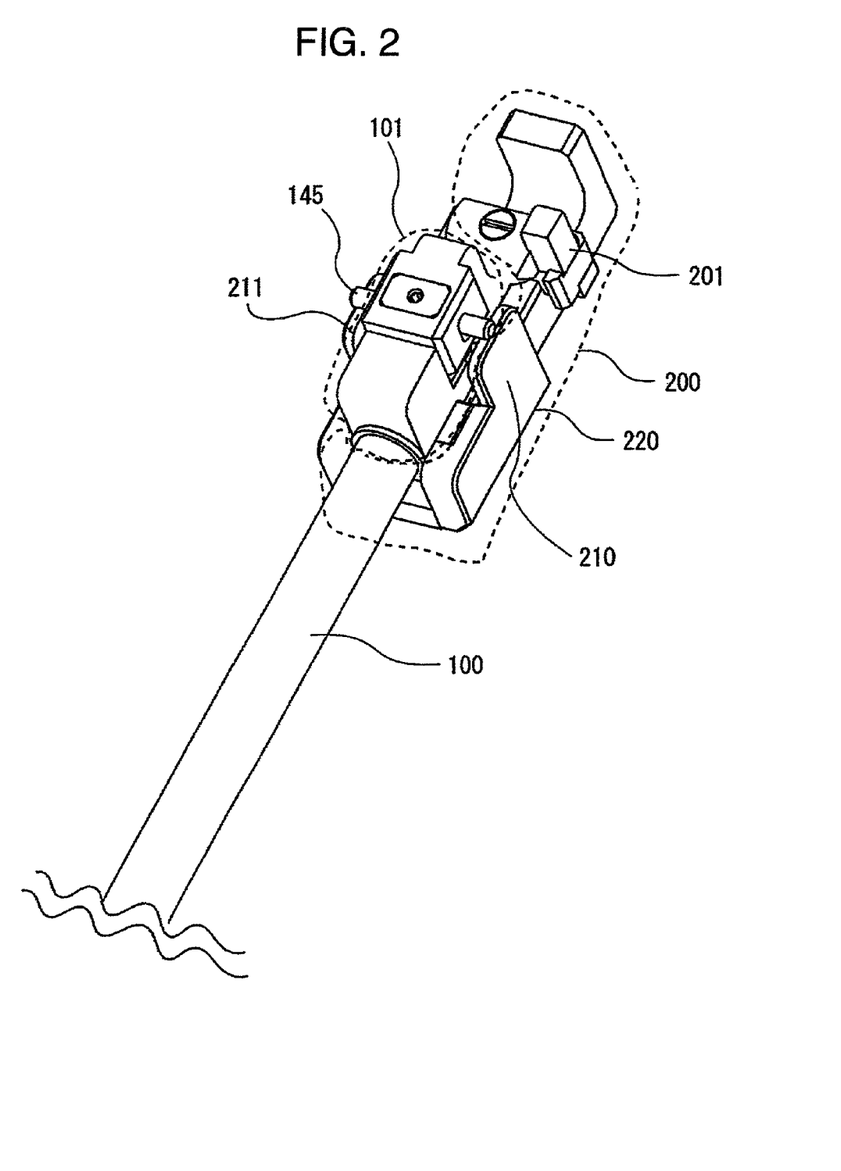
FIG. 2 is an enlarged view in the vicinity of a removable mechanism in the manipulation device in FIG. 1.

FIG. 2 shows an enlarged view in the vicinity of the removable mechanism 101. The removable mechanism 101 provided in the manipulator 100 is fitted to the removable driving mechanism 200, and the removable mechanism 101 is fixed by a lever 201 of the removable driving mechanism 200. Details of them are mentioned later.

Figure 3:
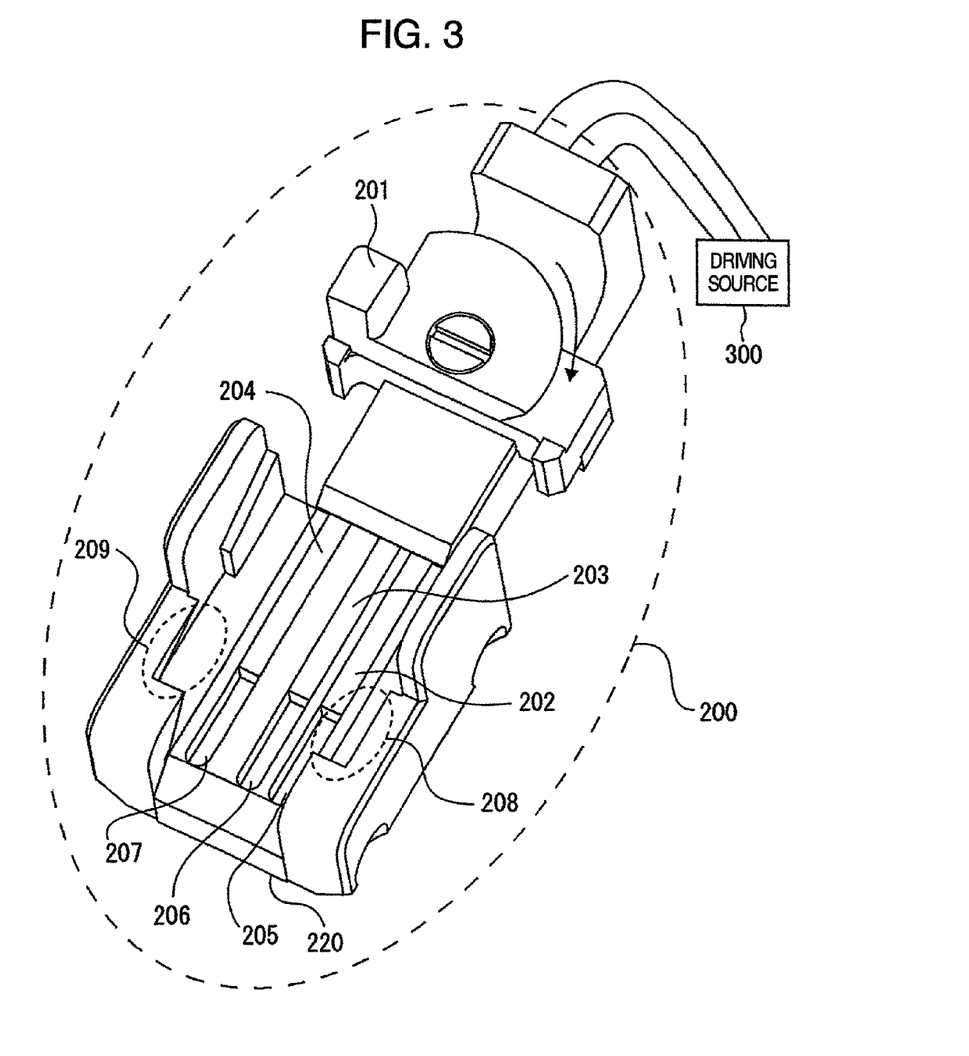
FIG. 3 is a perspective view of a removable driving mechanism in the manipulation device in FIG. 1.

FIG. 3 is a perspective view of the removable driving mechanism 200. The removable driving mechanism 200 is constituted by a base portion 220, a plurality of driving racks, a lever 201 and the like. A plurality of driving racks are constituted by a first driving rack 204, a second driving rack 203 and a third driving rack 202.

The base portion 220 has a plurality of driving rack grooves, left and right guide grooves 208 and 209, and left and right side walls 210 and 211. A plurality of driving rack grooves are constituted by a first driving rack groove 207, a second driving rack groove 206 and a third driving rack groove 205.

The first driving rack groove 207, the second driving rack groove 206 and the third driving rack groove 205 are formed in parallel to each other on an upper surface of a bottom wall of the base portion 220. Further, the first driving rack 204 is movably arranged within the first driving rack groove 207, the second driving rack 203 is arranged within the second driving rack groove 206, and the third driving rack 202 is arranged within the third driving rack groove 205. Each of the driving racks 202 to 204 is independently driven by a driving source 300, and is linearly moved in a groove direction within each of the rack grooves 205 and 207.

The left and right guide grooves 208 and 209 are provided for guiding the removable mechanism 101 to a predetermined position of the removable driving mechanism 200 at a time of connecting the removable mechanism 101 to the removable driving mechanism 200, and are provided so as to be positioned in both sides of the rack grooves 205 and 207 in the base portion 220 and in the manipulator side.

The left and right side walls 210 and 211 are provided for fixing the removable mechanism 101 connected to the removable driving mechanism 200, and are attached rotatably to the upper surface of the base portion 200 so as to be positioned in an opposite manipulator side in the base portion 200.

Figure 4:
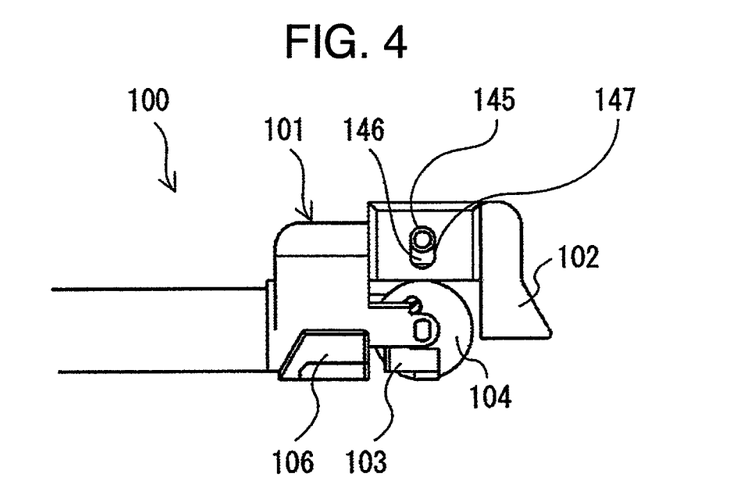
FIG. 4 is a side elevational view of the removable mechanism in the manipulation device in FIG. 1.
Figure 5:
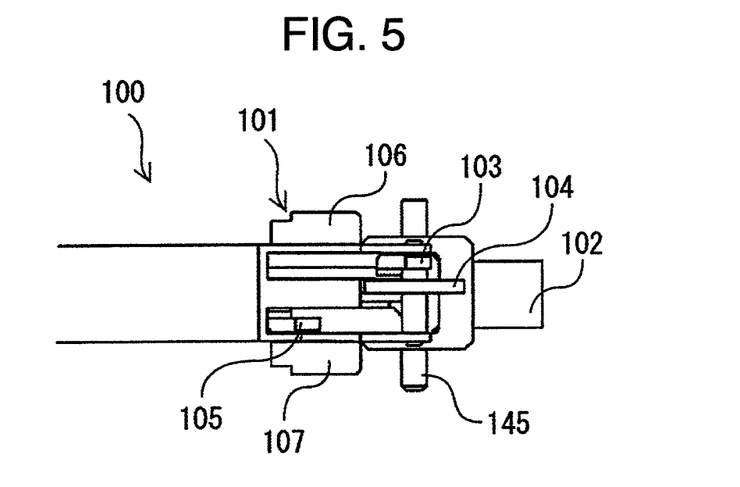
FIG. 5 is a bottom elevational view of the removable mechanism in the manipulation device in FIG. 1.

FIG. 4 is a side elevational view of the removable mechanism 101 provided in the manipulator 100, and FIG. 5 is a bottom elevational view of FIG. 4. The removable mechanism 101 has a plurality of contact devices, left and right guides 106 and 107, a fixing device 102, a lock cover 145, a lock rack 146 and a lock bar guide 147. A plurality of contact devices are constituted by a first contact rack 105, a contact gear 104 and a second contact rack 103.

The first contact rack 105, the contact gear 104 and the second contact rack 103 are provided in such a manner as to be capable of engaging with the first driving rack 204, the second driving rack 203 and the third driving rack 202 respectively at a time of connecting the removable mechanism 101 to the removable driving mechanism 200.

The left and right guides 106 and 107 have the same outer surface shapes as inner surface shapes of the left and right guide grooves 208 and 209, and are provided in both sides of the removable mechanism 101. The fixing device 102 is attached to a rear end surface of the removable mechanism 101, and is structured such as to be capable of being locked to the lever 201.

The cylindrical lock bar 145 passes through the lock rack 146 so as to protrude to both sides, and the both side protruding portions are arranged so as to move up and down within the lock bar guide 147. The lock rack 146 is arranged so as to be movable up and down in accordance with a vertical motion of the lock bar 145, and a lower surface thereof forms a cogged surface. When the lock rack 146 is moved down, the cogged surface in the lower surface engages with the contact gear 104, and the engagement is canceled at a time when the lock rack 146 is moved up.

Figure 6:
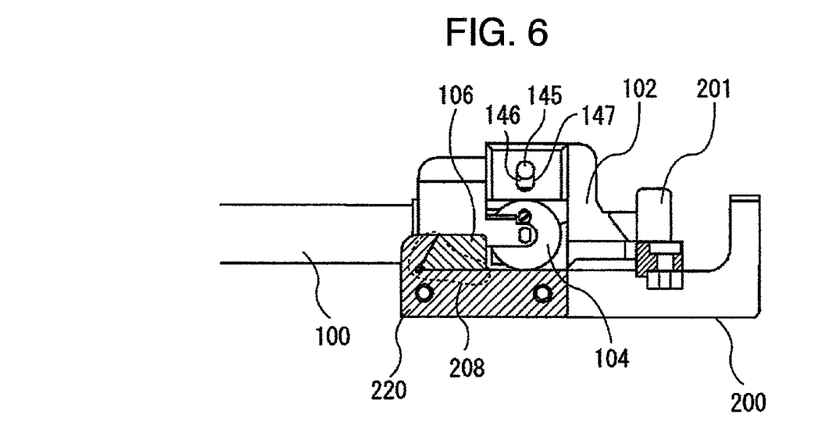
FIG. 6 is a cross sectional view showing a connected state of the removable mechanism and the removable driving mechanism in the manipulation device in FIG. 1.
Figure 7:
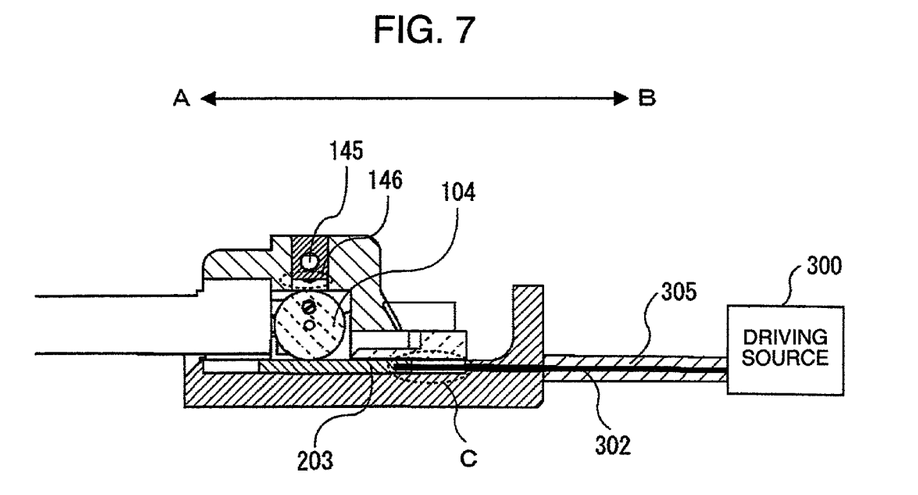
FIG. 7 is a cross sectional view showing a connected state of a second driving rack and a contact gear in the manipulation device in FIG. 1.
Figure 8:
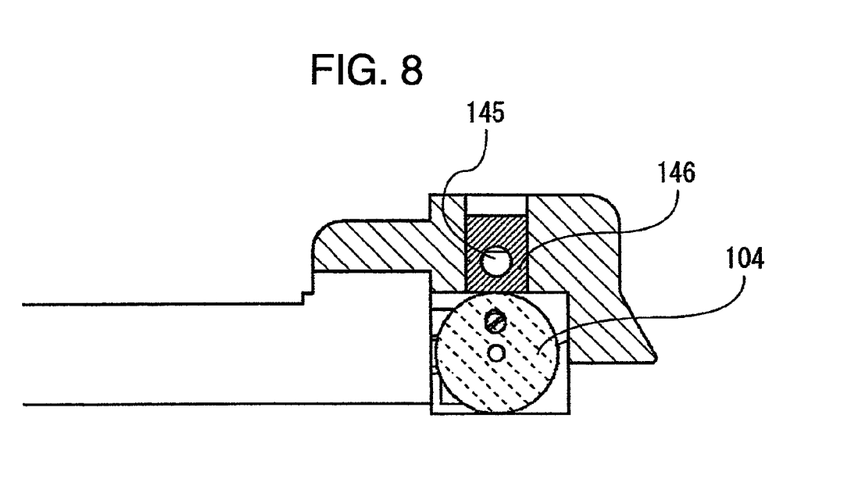
FIG. 8 is a cross sectional view showing a locked state of the contact gear in the manipulation device in FIG. 1.

FIG. 6 is a cross sectional view showing a connected state between the removable mechanism 101 and the removable driving mechanism 200, FIG. 7 is a cross sectional view showing a connected state between the second driving rack 203 and the contact gear 104, and FIG. 8 is a cross sectional view showing a lock state of the contact gear 104.

The connection between the removable mechanism 101 and the removable driving mechanism 200 is carried out by inserting the left and right guides 106 and 107 to the left and right guide grooves 208 and 209, rotating the lever 201 in a direction of an arrow in FIG. 3, and pressing the lever 201 against the fixing device 102 as shown in FIG. 6. It is possible to constrain the manipulator 100 by holding the fixing device 102 by the lever 201 as mentioned above, and the removable mechanism 101 can be attached and detached in accordance with such an easy method as the rotation of the lever 201. Further, it is possible to easily discriminate whether or not the manipulator is securely fixed, by viewing the direction of the lever 201, and it is possible to prevent a falling accident of the manipulator 100 caused by an uncertain fixation.

The driving force is transmitted from the removable driving mechanism 200 to the manipulator 100 on the basis of an engagement between the first contact rack 105 provided in the removable mechanism 101 and the first driving rack 204, an engagement between the contact gear 104 and the second driving rack 203, and an engagement between the second contact track 103 and the third driving rack 202.

As shown in FIG. 7, the contact gear 104 is engaged with the second driving rack 203. The second driving rack 203 is connected a driving apparatus side rod 302 having a flexibility. The driving apparatus side rod 302 passes through a driving apparatus side tube 305 having a flexibility. It is possible to linearly move the second driving rack 203 in a direction A-B by fixing the driving apparatus side tube 305, and linearly moving the driving apparatus side rod 302 in the direction A-B by the driving source 300. The linear motion of the second driving rack 203 is converted into a rotating motion by the contact gear 104. As mentioned above, by using the driving apparatus side rod 302, it is possible to avoid a deterioration of a controllability caused by a slack or the like, in comparison with a driving transmission by a wire or the like. Further, in the case of the wire, a fatigue breakage frequently comes into question, however, in the case of the rod, the fatigue breakage is hard to be generated. Further, at a time of transmitting the linear motion and the rotating motion, at least two wires are generally necessary in the case of the wire, however, in the case of the rod, it is possible to transmit the linear motion by one rod, thereby contributing to a downsizing, an improvement of a maintenance performance and the like.

In this case, in the driving force transmission between the first driving rack 204 and the driving source 300, and the driving force transmission between the third driving rack 202 and the driving source 300, there is employed the same structure as the driving force transmission between the second driving rack 203 and the driving source 300 mentioned above.

At a time of attaching the removable mechanism 101 to the removable driving mechanism 200, there is a possibility that the contact gear 203 is unexpectedly rotated from the initial state. Accordingly, in the present embodiment, it is possible to prevent the contact gear 104 from being unexpectedly rotated by fixing the contact gear 104 by moving the lock bar 145 along the lock bar guide 147, and pressing the lock rack 146 against the contact gear 104 as shown in FIG. 8 so as to engage the cogged surface of the lock rack 146 with the cogged surface of the contact gear 104.

Further, at a time of attaching the removable mechanism 101 to the removable driving mechanism 200, the lock bar 145 comes into contact with the side wall 210 and the side wall 211 as shown in FIG. 2, and is pushed up along the lock bar guide 147. Accordingly, as shown in FIG. 7, the lock rack 146 and the contact gear 104 are not engaged with each other, and it is possible to rotate the contact gear 104 by the driving source 300. It is possible to prevent such an accident as to neglect canceling the fixation of the contact rack 104 or the like, by a mechanism by which the lock rack 146 does not automatically engage with the contact gear 104 at a time of attaching.

In order to downsize the removable driving mechanism 200, and prevent a buckling of the removable driving mechanism 200 in a portion C (refer to FIG. 7) of the driving apparatus side rod 302, the linear moving amounts of the first driving rack 204, the second driving rack 203 and the third driving rack 202 are limited. Accordingly, in the case that a great linear moving amount is necessary in the manipulator 100, it is necessary to amplify the linear moving amount from the removable mechanism 101 of the linear moving manipulator 100 to the manipulator leading end portion 118.

Figure 9:
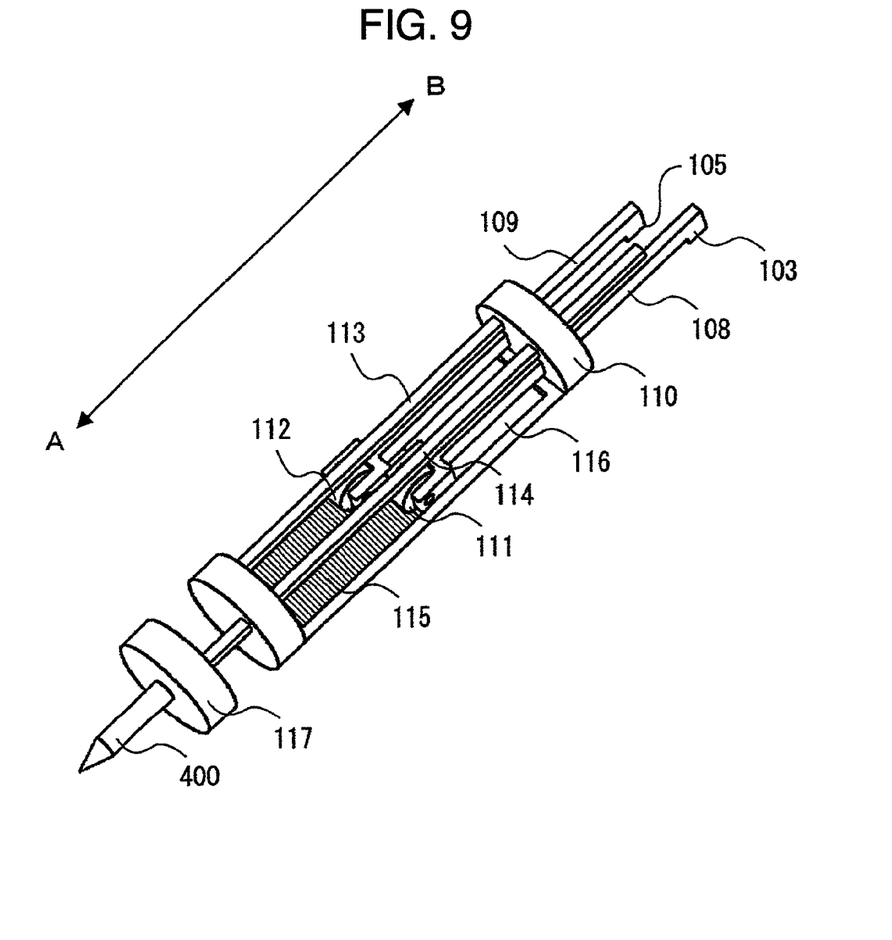
FIG. 9 is a schematic view of a mechanism amplifying a linear moving amount of a manipulator in the manipulation device in FIG. 1.
Figure 10:
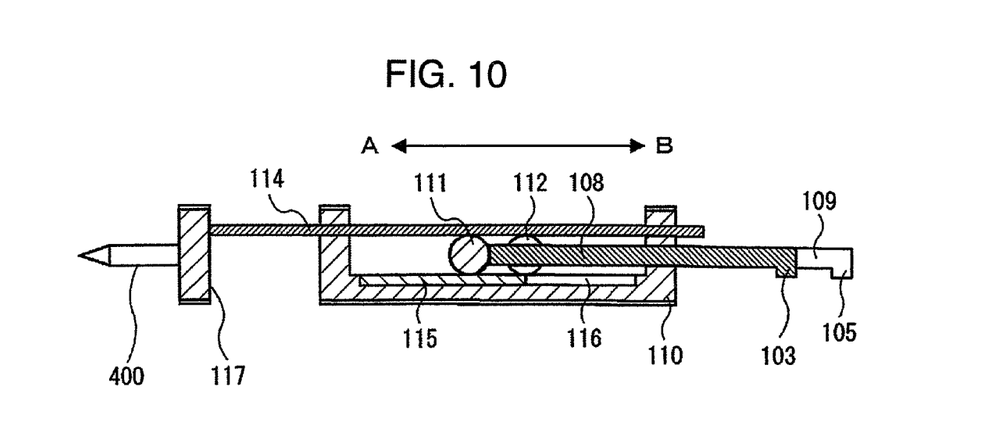
FIG. 10 is a cross sectional view of the translational speed enhancement mechanism in FIG. 9.

FIG. 9 is a schematic view of a mechanism amplifying the linear moving amount in the manipulator 100, and FIG. 10 is a cross sectional view of the translational speed enhancement mechanism in FIG. 9. In this case, the manipulator bending portion 119 is omitted for simplifying the drawing, in FIG. 9.

In FIG. 9, the first rod 109 connected to the first contact rack 105 is supported to the manipulator shaft portion 110 so as to be linearly movable in the direction A-B. The second rod 108 connected to the second contact rack 103 is supported to the manipulator shaft portion 110 so as to be linearly movable in the direction A-B. The second rod 108 and the first rod 109 are arranged in parallel.

The fixed rack (the first rack) 113 is fixed to the manipulator shaft portion 110, and is engaged with the first gear 112. The output rack (the third rack) 114 is supported to the manipulator shaft portion 110 so as to be linearly movable in the direction A-B, and is engaged with the second gear 111.

The first gear 112 is supported to the first rod 109 by its shaft, and is engaged with the transmission rack 115 so as to be rotatable. The second gear 111 is supported to the second rod 108 by its shaft, and is engaged with the transmission rack (the second rack) 115 so as to be rotatable.

The transmission rack 115 is arranged within the transmission rack groove 116 formed in the manipulator shaft portion 110 so as to be long in the direction A-B, and is linearly moved in the direction A-B along the transmission rack shaft 116. The first gear 112 is pinched between the fixed rack 113 and the transmission rack 115, and is arranged in a state of being engaged with each of the fixed rack 113 and the transmission rack 115. Further, the second gear 111 is pinched between the transmission rack 115 and the output rack 114 as shown in FIG. 10, and is arranged in a state of being engaged with each of the transmission rack 115 and the output rack 114.

A handle 117 is fixed to a leading end of the output rack 114 as shown in FIG. 9, and a needle 400 is attached to the handle 117 in a replaceable manner.

Figure 11A:
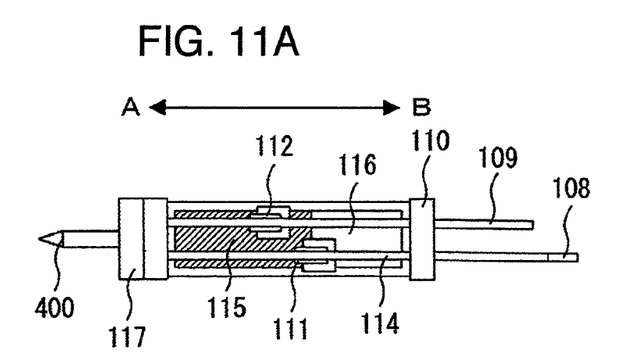
FIGS. 11A to and 11C are views for explaining a motion of the translational speed enhancement mechanism.
Figure 11B:
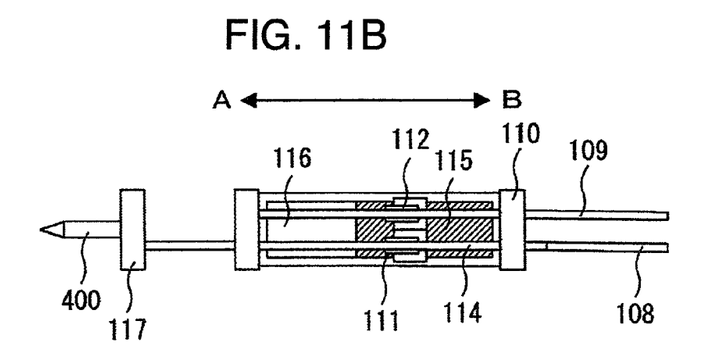
Figure 11C:
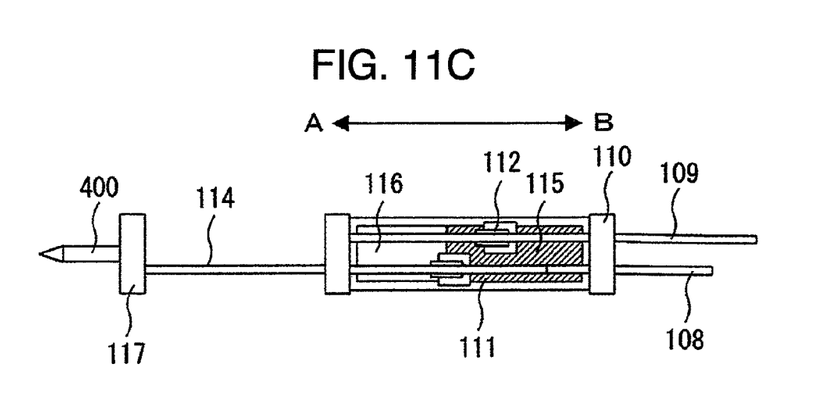

FIG. 11 is a view explaining a motion of the translational speed enhancement mechanism in FIG. 9. FIG. 11A shows a reference state of the translational speed enhancement mechanism, FIG. 11B shows a one-stage amplified state of the translational speed enhancement mechanism, and FIG. 11C shows a two-stage amplified state of the translational speed enhancement mechanism, respectively.

First of all, it the first rod 109 is linearly moved in the direction B in the state of FIG. 11A, the first gear 112 is moved in the direction B together with the first rod 109 while rotating. Accordingly, the transmission rack 115 engaged with the first gear 112 is exposed to both of a driving force in the direction B caused by the rotation of the first gear 112 and a driving force in the direction B caused by the movement of the first gear 112, and is linearly moved along the transmission rack groove 116 in the direction B at a moving amount which is twice as much as the linear moving amount of the first rod 109. At this time, if the second rod 108 is set to the fixed state, the second gear 111 is rotated on the basis of a linear movement of the transmission rack 115. On the basis of this rotation, the output rack 114 is linearly moved in the direction A at an equal moving amount to a moving amount of the transmission rack 115. Accordingly, the output rack 114 is linearly moved in a needle point direction at a moving amount which is twice as much as the moving amount of the first rod 109, as shown in FIG. 11B.

Next, if the first rod 109 is fixed and the second rod 108 is linearly moved in the direction A (the needle point direction), in a state of FIG. 11B, the second gear 111 is moved in the direction A together with the second rod 108 while rotating. Accordingly, the output rack 114 engaging with the second gear 111 is exposed to both the driving force in the direction A caused by the rotation of the second gear 111 and the driving force in the direction A caused by the movement of the second gear 111, and is linearly moved in the direction A at a moving amount which is twice as much as the linear moving amount of the second rod 108, as shown in FIG. 11C.

In this case, the motion mentioned above is explained on the basis of the example in which the second rod 108 is first fixed so as to linearly move the first rod 109, and the first rod 109 is next fixed so as to linearly move the second rod 108, however, the same effect can be obtained even if the moving orders of the second rod 108 and the first rod 109 are inverted. Further, the second rod 108 and the first rod 109 may be simultaneously moved linearly. In this case, it is possible to obtain a large moving amount for a short operating time.

Further, the translational speed enhancement mechanism is driven by the driving source 300 such as the motor or the like via the removable driving mechanism 200, however, may be driven by a manual driving source. Alternatively, the second rod 108 and the first rod 109 may be directly driven by the driving source such as the motor or the like, or manually. In the case of being driven manually, even if a moving amount of a human finger or the like is small, a large linear moving amount can be obtained, and there is an advantage that an operability is good.

Further, the number of the driving rack provided in the removable driving mechanism 200 is not limited to three including the first driving rack 204, the second driving rack 203 and the third driving rack 202, but may have a necessary number of driving racks required by the manipulator having the maximum degree of freedom in a plurality of replaced manipulators. In this case, the removable driving mechanism 200 can correspond to various manipulators by unifying the removable mechanism 101 of the replaced manipulator 100.

Further, the embodiment mentioned above uses two driving racks including the first driving rack 204 and the third driving rack 202, for the mechanism amplifying the linear moving amount, however, it is possible to use one to a plurality of driving racks without being limited to two driving racks. At a time of using only one driving rack, in the embodiment mentioned above, the transmission rack 115 is set to a fixed rack fixed to the manipulator shaft portion 110, and only the set of the second gear 111, the output rack 114 and the second rod 108 may be used. At this time, it is possible to linearly move the output rack at the linear moving amount which is twice as much as the linear moving amount of the second rod 108. Further, at a time of using three driving racks, in the embodiment mentioned above, it is preferable that the output rack 114 is set to a new transmission rack, and is connected to a third gear connected to the third rod, and the new output rack is provided in the third gear. At this time, it is possible to linearly move the output rack at a total moving amount obtained by doubling each of the moving amounts of three rods. Further, it is preferable to arrange plural sets of mechanisms each constituted by the transmission rack 115, the second rod 108, the second gear 11 and the output rack 114.

The mechanism amplifying the linear moving amount in accordance with the present embodiment is constituted by the gear and the rack, and does not use any wire. Accordingly, it is possible to avoid the fatigue disconnection, the slack or the like of the wire, and a maintenance performance is improved. Further, it is possible amplify the linear moving amount regardless of a magnitude of a diameter of the gear.

Further, in the case of amplifying the moving amount of the linear motion generally obtained by one driving mechanism, the driving force required by one driving mechanism is increased at an equal rate to an amplification factor of the linear moving amount, at a time of outputting a predetermined force. However, in the present embodiment, in the case of utilizing a plurality of driving hooks, it is possible to disperse the driving force required for linearly moving the output rack into a plurality of driving mechanisms. At a time of outputting the predetermined force, in the case of dispersing the driving force into a plurality of driving mechanisms, the driving force required by one driving mechanism corresponds to a value obtained by dividing the amplification factor of the linear moving amount by the number of the driving mechanisms.

In this case, the mechanism amplifying the linear moving amount in accordance with the present embodiment employs the gears and the racks, however, may employ rollers and plates which come into rolling contact with each other.

Figure 12:
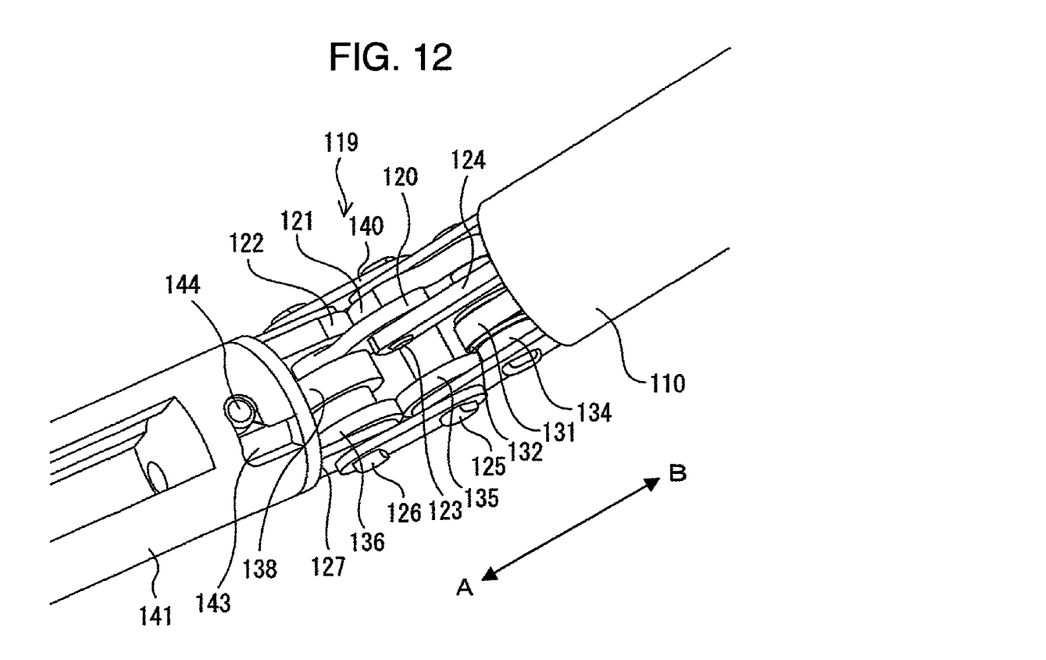
FIG. 12 is an enlarged view of a manipulator bending portion in the manipulation device in FIG. 1.
Figure 13A:
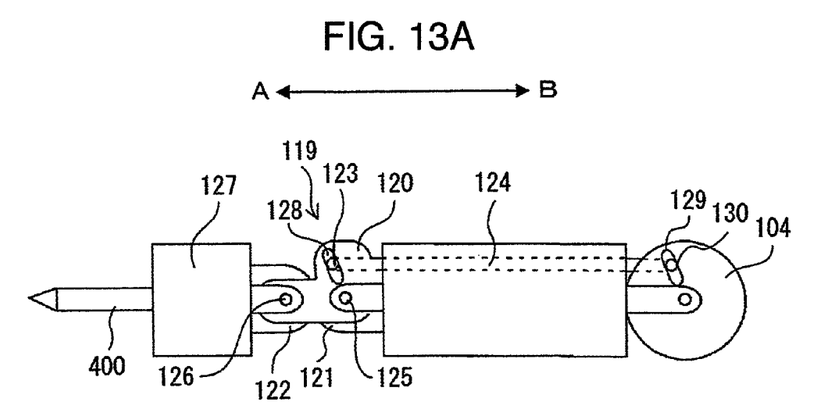
FIGS. 13A and 13B are views for explaining a motion of a bending mechanism in the manipulator bending portion in FIG. 12.
Figure 13B:
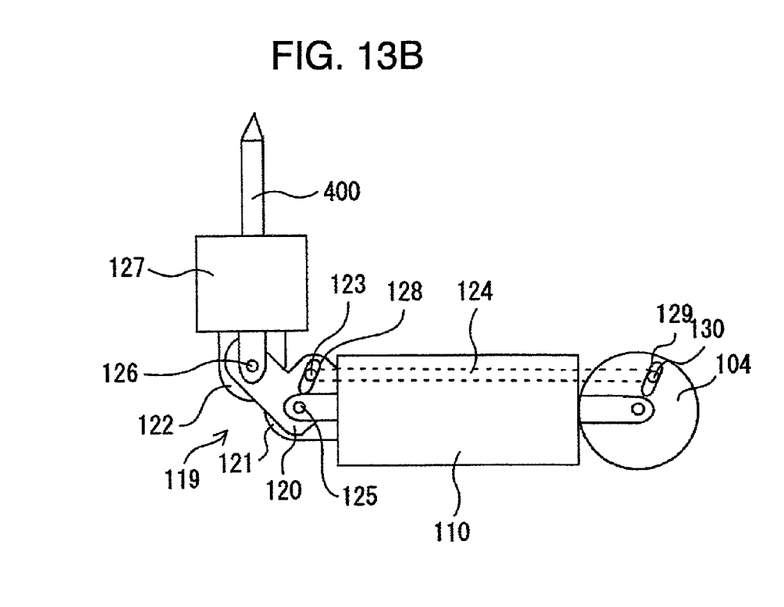

FIG. 12 is an enlarged view of the manipulator bending portion 119 in FIG. 1, and FIG. 13 is a view explaining a motion of the bending mechanism in the manipulator bending portion 119 in FIG. 12. In this case, FIG. 13A shows a reference state in which the manipulator bending portion 119 is in a linear shape, and FIG. 13B shows a state in which the manipulator bending portion 119 is vertically bent, respectively.

The bending of the manipulator is carried out by bending the leading end side base portion 127 with respect to the manipulator shaft portion 110 by a bending mechanism using a bending plate 120, fixed gears 121 and 122, a pin 123, a bending link 124 and pins 125 and 126.

The fixed gear 121 is fixed to the manipulator shaft portion 110 around the pin 125. Further, the fixed gear 122 is fixed to the leading end side base portion 127 around the pin 126. In this case, the fixed gear 121 and the fixed gear 122 are set in an engaged state. Further, the pin 125 is rotatably supported to the manipulator shaft portion 110, and the pin 126 is rotatably supported to the leading end side base portion 127. The pins 125 and 126 pass through the bending plate 120 so as to be rotatably constrained. Further, the bending plate 120 is provided with a long hole 129 in such a manner that the pin 123 fixed to the bending link 124 can slide. In this case, the bending link 124 is supported to the manipulator shaft portion 110 so as to be freely movable linearly with respect to the direction A-B.

The contact gear 104 is provided with the long hole 129 in such a manner that the pin 130 fixed to the bending link 124 can slide in the same manner as the long hole 129. If the rotating motion is applied to the contact gear 104 by the second driving rack 203, the bending link 124 only move linearly as shown in FIG. 13B because the bending link 124 is supported so as to be movable linearly with the manipulator shaft portion 110 in the direction A-B, and the rotating force is transmitted to the bending plate 120. Since the bending plate 120 is rotated around the pin 125, the leading end side base portion 127 constrained so as to be rotatable with the pin 126 is rotated. At this time, since the fixed gear 122 connected to the leading end side base portion 127 is engaged with the fixed gear 121 connected to the manipulator shaft portion 110, the leading end side base portion 127 is rotated around the pin 126 in accordance with the rotation of the bending plate.

Since the bending link 124 carried out only the linear motion, it is not necessary to prepare a space for the vertical motion of the bending link 124, in comparison with the case that the pin 123 and pin 130 fixed to the bending link 124 are rotatably constrained to the bending plate 120 and the contact gear 104 respectively, and the rotating force is transmitted by the parallel link structure, thereby contributing the downsizing of the mechanism. Further, it is possible to make a width of the link thick by utilizing the space of the vertical motion, and it is possible to transmit the greater force.

In this case, in the present embodiment, the fixed gears 121 and 122 are used, however, it is possible to use any contact member which comes into rolling contact without slipping.

Figure 14A:
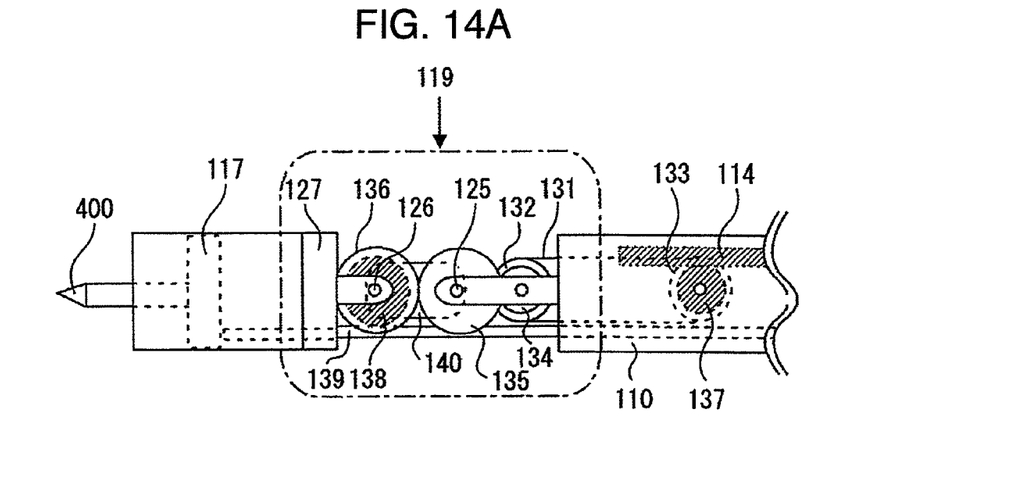
FIGS. 14A and 14B are views for explaining a motion of a transmission mechanism for bending of the manipulator bending portion in the manipulation device in FIG. 1.
Figure 14B:
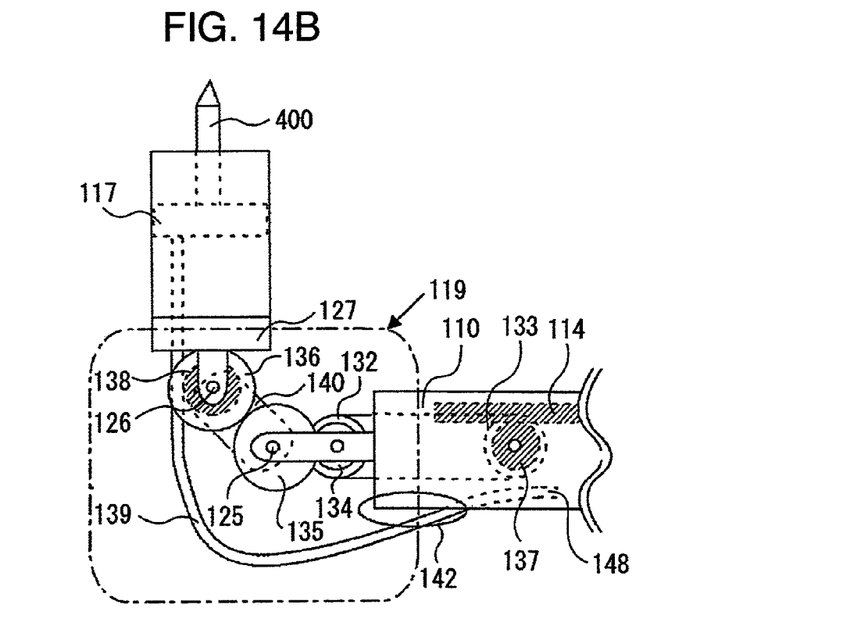

FIG. 14 is a view explaining the motion of the transmission mechanism for bending in the manipulator bending portion 119. The transmission mechanism for bending is a mechanism transmitting the linear motion of the output rack 114 via the manipulator bending portion 119, and linearly moving the needle 400 stored in the leading end of the manipulator 100.

FIG. 14A shows a state in which the manipulator bending portion 119 is in a linear shape. Further, a linear motion of the output rack 114 in FIG. 14A is converted into the rotating motion by a linear motion transmitting gear 137. A pulley 133 rotating synchronously with the liner moving transmission gear 137 is arranged coaxially with the linear motion transmitting gear 137. The rotating motion of the pulley 133 is transmitted to a pulley 132 by a timing belt 131. A linear motion transmitting gear 134 rotating synchronously with the pulley 132 is arranged coaxially with the pulley 132. The linear motion transmitting gear 134 is engaged with a linear motion transmitting gear 135 rotating around the pin 125, and the linear motion transmitting gear 135 is engaged with the linear motion transmitting gear 136. In this case, the linear motion transmitting gear 135 has an equal diameter to that of the fixed gear 121, and the linear motion transmitting gear 136 has an equal diameter to that of the fixed gear 122. A resin rack gear 138 rotating synchronously with the linear motion transmitting gear 136 is arranged coaxially with the linear motion transmitting gear 136. Accordingly, the rotating motion converted from the output rack 114 is transmitted to the resin rack gear 138. The rotating motion of the resin rack gear 138 is again converted into the linear motion by the resin rack 139. Further, the resin rack 139 is fixed to the handle 117 and the needle 400 is attached thereto in a replaceable manner. The handle 117 can move linearly in the leading end direction of the needle 400 in an inner portion of a needle guide 141 shown in FIG. 15. Accordingly, it is possible to linear move the needle 400 on the basis of the linear motion of the output rack 114.

FIG. 14B shows a state in which the manipulator bending portion 119 is vertically bent. Since the linear motion transmitting gear 135 has an equal diameter to that of the fixed gear 121, and the liner motion transmitting gear 136 has an equal diameter to that of the fixed gear 122, the linear motion transmitting gear 136 and the leading end side base portion 127 are equally rotated around the pin 126 at a time of bending, and a relative angle between the linear motion transmitting gear 136 and the leading end side base portion 127 is not changed. Accordingly, in the case of carrying out only the bending, the resin rack 139 is not driven, and the bending motion and the linear motion are not interfered.

As shown in FIG. 14B, a resin rack end surface 148 in a side which is not fixed to the handle 117 of the resin rack 139 is stored in the inner portion of the manipulator shaft portion 110, and is structured such as to have no effect on a peripheral environment such that the other internal organ, blood vessel or the like than the affected portion is not injured by the end of the resin rack 139. A notch 142 is provided in a lower portion of the manipulator shaft portion 110, in such a manner as to store the resin rack 139 in the inner portion of the manipulator shaft portion 110 with a suitable radius of curvature as shown in FIG. 14B, even at a time of bending in the manipulator bending portion 119.

Figure 15:
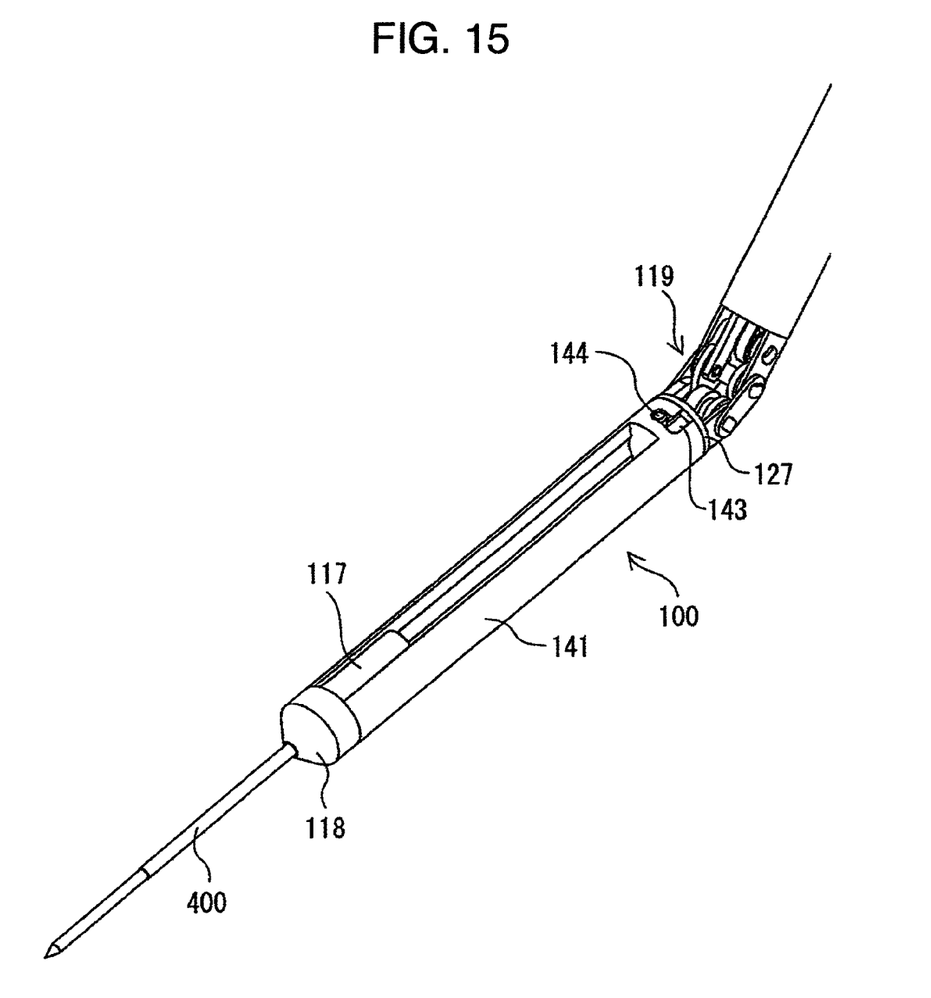
FIG. 15 is an enlarged view in the vicinity of a needle guide in the manipulation device in FIG. 1.

FIG. 15 shows an enlarged view in the vicinity of the needle guide 141 in the present embodiment. An attaching groove 143 is provided in the needle guide 141. The needle guide 141 is fixed to the leading end side base portion 127 in such a manner as to be easily attached and detached, by fitting a fixed pin 144 fixed to the leading end side base portion 127 to the attaching groove 143. It is possible to regulate a length from the manipulator bending portion 119 to the manipulator leading end portion 118 by attaching a structure obtained by changing a length with respect to the leading end direction of the needle 400 of the needle guide 141, in correspondence to its purpose. Further, the manipulator leading end portion 118 is formed as a conical shape as shown in FIG. 11, and is structured such as to broaden the view of a portion to which the needle is stuck at a time of boring the needle.

In accordance with the present embodiment, it is possible to achieve the narrow manipulator which can carry out such a treatment as to insert the end-effecter while avoiding the obstacle within the human body, while having a large moving amount of the leading end. Further, it is possible to construct the manipulation device which can attach and detach the manipulator in the replaceable manner, is structured as a general purpose manner which can be driven by the removable driving mechanism, and can carry out the multifunction treatment with the removable mechanism having both the maintenance performance and the controllability.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A manipulator comprising:
a manipulator shaft portion;
a first rod supported so as to be capable of linearly moving with respect to said manipulator shaft portion and driven by a driving force;
a first gear rotatably supported to said first rod and moved in accordance with a movement of said first rod;
a first rack fixed to said manipulator shaft portion;
a second rack supported so as to be capable of linearly moving in the same direction as said first rod with respect to said manipulator shaft portion;
an end-effecter driven by the driving force generated in accordance with a movement of said second rack,
a second rod supported so as to be capable of linearly moving with respect to said manipulator shaft portion and driven by the driving force,
a second gear rotatably supported to said second rod, and
a third rack supported so as to be capable of linearly moving in the same direction as said second rod with respect to said manipulator shaft portion,
wherein said first rack and said second rack are arranged in parallel in such a manner that a cogged surface of said first rack and a cogged surface of said second rack come face to face, and said first gear is pinched between said first rack and said second rack, and is arranged in a state of engaging with each of said first rack and said second rack, and
wherein said second rack and said third rack are arranged in parallel in such a manner that a cogged surface of said second rack and a cogged surface of said third rack come face to face, said second gear is pinched between said second rack and said third rack, and is arranged in a state of engaging with each of said second rack and said third rack, and said end-effecter is driven by a driving force generated in accordance with the movement of said third rack.

2. A manipulator as claimed in claim 1, wherein plural sets of mechanisms are provided in line, the mechanism comprising said second rack, said second rod, said second gear and said third rack.

3. A manipulator as claimed in claim 1, wherein a manipulator bending portion bending said manipulator is provided in an intermediate portion of said manipulator, and said manipulator bending portion has a transmission mechanism for bending drivingly transmitting the linear motion by said second rack to a leading end portion of said manipulator via said manipulator bending portion.

4. A manipulator comprising:
a manipulator shaft portion;
a first rod supported so as to be capable of linearly moving with respect to said manipulator shaft portion and driven by a driving force;
a first gear rotatably supported to said first rod and moved in accordance with a movement of said first rod;
a first rack fixed to said manipulator shaft portion;

a second rack supported so as to be capable of linearly moving in the same direction as said first rod with respect to said manipulator shaft portion; and an end-effecter driven by the driving force generated in accordance with a movement of said second rack, wherein said first rack and said second rack are arranged in parallel in such a manner that a cogged surface of said first rack and a cogged surface of said second rack come face to face, and said first gear is pinched between said first rack and said second rack, and is arranged in a state of engaging with each of said first rack and said second rack, and wherein a manipulator bending portion bending said manipulator is provided in an intermediate portion of said manipulator, and said manipulator bending portion has a transmission mechanism for bending drivingly transmitting the linear motion by said second rack to a leading end portion of said manipulator via said manipulator bending portion.

5. A manipulator as claimed in claim 4, wherein said transmission mechanism for bending has a first linear motion transmitting gear converting the linear motion by said second rack into a rotating motion, a first pulley provided coaxially with said first linear motion gear and synchronously rotating with said first linear motion transmission gear, a timing belt transmitting the rotating motion of said first pulley to the second pulley, a second linear motion transmitting gear provided coaxially with said second pulley and synchronously rotating with said second pulley, a third linear motion transmission gear provided so as to be engaged with said second linear motion transmitting gear, a fourth linear motion transmitting gear provided so as to be engaged with said third linear motion transmitting gear, a rack gear provided coaxially with said fourth linear motion transmitting gear, rotating synchronously with said linear motion transmitting gear and having a flexibility, and a rack converting the rotating motion of said rack gear having the flexibility into the linear motion so as to generate the driving force applied to said end-effecter and having a flexibility.

6. A manipulator as claimed in claim 4 or 5, wherein the leading end portion of said manipulator is replaceable.

7. A manipulation device comprising:
a manipulator; and
a driving apparatus driving said manipulator,
wherein said manipulator comprises:
a manipulator shaft portion;
a first rod supported so as to be capable of linearly moving with respect to said manipulator shaft portion and driven by a driving force of said driving apparatus;
a first gear rotatably supported to said first rod and moved in accordance with a movement of said first rod;
a first rack fixed to said manipulator shaft portion;
a second rack supported so as to be capable of linearly moving in the same direction as said first rod with respect to said manipulator shaft portion; and
an end-effecter driven by the driving force generated in accordance with a movement of said second rack, and wherein said first rack and said second rack are arranged in parallel in such a manner that a cogged surface of said first rack and a cogged surface of said second rack come face to face, and said first gear is pinched between said first rack and said second rack, and is arranged in a state of engaging with each of said first rack and said second rack, wherein a removable mechanism is provided in a manipulator side, a removable driving mechanism is provided in a driving apparatus side, and the removable mechanism in said manipulator side is detachable with respect to the removable driving mechanism in said driving apparatus side, and wherein said manipulator is provided with a second rod supported so as to be capable of linearly moving with respect to said manipulator shaft portion and driven by the driving force, a second gear rotatably supported to said second rod, and a third rack supported so as to be capable of linearly moving in the same direction as said second rod with respect to said manipulator shaft portion, wherein said second rack and said third rack are arranged in parallel in such a manner that a cogged surface of said second rack and a cogged surface of said third rack come face to face, said second gear is pinched between said second rack and said third rack, and is arranged in a state of engaging with each of said second rack and said third rack, and said end-effecter is driven by a driving force of said third rack.

8. A manipulator as claimed in claim 3, wherein said transmission mechanism for bending has a first linear motion transmitting gear converting the linear motion by said second rack into a rotating motion, a first pulley provided coaxially with said first linear motion gear and synchronously rotating with said first linear motion transmission gear, a timing belt transmitting the rotating motion of said first pulley to the second pulley, a second linear motion transmitting gear provided coaxially with said second pulley and synchronously rotating with said second pulley, a third linear motion transmission gear provided so as to be engaged with said second linear motion transmitting gear, a fourth linear motion transmitting gear provided so as to be engaged with said third linear motion transmitting gear, a rack gear provided coaxially with said fourth linear motion transmitting gear, rotating synchronously with said linear motion transmitting gear and having a flexibility, and a rack converting the rotating motion of said rack gear having the flexibility into the linear motion so as to generate the driving force applied to said end-effecter and having a flexibility.

9. A manipulator as claimed in claim 3 or 8, wherein the leading end portion of said manipulator is replaceable.

* * * * *